(12) United States Patent
Lee

(10) Patent No.: US 7,520,868 B2
(45) Date of Patent: Apr. 21, 2009

(54) DELIVERY APPARATUS FOR MEDICAL FLUIDS IN FLAT AND ROUND SHAPE

(75) Inventor: Jong Woo Lee, Seoul (KR)

(73) Assignee: Acemedical Co., Ltd., Koyang (KR)

( * ) Notice: Subject to any disclaimer, the term of this patent is extended or adjusted under 35 U.S.C. 154(b) by 0 days.

(21) Appl. No.: 10/822,592

(22) Filed: Apr. 12, 2004

(65) Prior Publication Data

US 2005/0075604 A1 Apr. 7, 2005

(30) Foreign Application Priority Data

Oct. 7, 2003 (KR) .................... 10-2003-0069688

(51) Int. Cl.
*A61M 37/00* (2006.01)
(52) U.S. Cl. .................. 604/132; 604/131; 604/890.1
(58) Field of Classification Search ............. 604/890.1, 604/891.1, 131, 132, 533, 93.01, 151, 153, 604/212, 246, 257, 259
See application file for complete search history.

(56) References Cited

U.S. PATENT DOCUMENTS

| | | | |
|---|---|---|---|
| 3,217,949 A | * | 11/1965 | Davis .................. 222/480 |
| 3,980,083 A | | 9/1976 | Elliott |
| 4,318,400 A | | 3/1982 | Peery et al. |
| 4,411,652 A | | 10/1983 | Kramer et al. |
| 4,741,733 A | | 5/1988 | Winchell et al. |
| 4,904,239 A | | 2/1990 | Winchell et al. |
| D324,911 S | | 3/1992 | Sancoff et al. |
| 5,176,360 A | | 1/1993 | Winchell et al. |
| 5,830,186 A | | 11/1998 | Gonzales et al. |
| 5,846,216 A | | 12/1998 | Gonzales |
| 5,957,890 A | * | 9/1999 | Mann et al. .................. 604/131 |
| 6,024,724 A | * | 2/2000 | Lee .......................... 604/132 |
| 6,908,452 B2 | * | 6/2005 | Diaz et al. .................. 604/131 |

\* cited by examiner

*Primary Examiner*—Kevin C Sirmons
*Assistant Examiner*—Laura C Schell
(74) *Attorney, Agent, or Firm*—Jordan and Hamburg LLP

(57) ABSTRACT

A medical fluid delivery apparatus for the discharge of a specific and constant volume of medical fluids includes a two-layered tubular body that is wound on a projecting holder, which reduces the change in expansion pressure. Having the tubular body wound up enables a variety in design. The utilization of an intermediate ring enables a variety of products just by exchanging the intermediate ring to provide different capacity volumes of the tubular body.

18 Claims, 7 Drawing Sheets

DELIVERY APPARATUS FOR MEDICAL FLUIDS IN FLAT AND ROUND SHAPE

BACKGROUND OF THE INVENTION

This invention relates to a medical apparatus, and, more particularly, to a device for delivering a specific volume of medical fluid via a tube.

Existing delivery apparatus for medical fluids utilizing tubes allow delivery of medical fluids by the expansion pressure of a tubular body which is inserted into a pipe-conduit having channels and which expands when medical fluid is injected.

However, its disadvantages are that delivery of a specific volume of medical fluid is impossible since such expansion results in different expansion pressure for the beginning and later periods of fluid delivery, and also because of being configured as a pipe-conduit, and thereby manufactured in an elongated shape, it is inconvenient to carry as it dangles loosely.

BRIEF SUMMARY OF THE INVENTION

The present invention seeks to overcome these problems in the prior art by providing a tubular-body, which when wound circularly, is reduced in size to a circular shape that maintains constant pressure both in the beginning and later periods of a fluid delivery. Also because it is manufactured in a flat and round shape, it is easy to carry.

The present invention is a delivery apparatus for medical fluids, which utilizes a tubular body, wherein the tubular body is wound and fixed on a projecting holder and maintains the expansion pressure of the expanding tubular body the same for the beginning and later periods of fluid delivery, and has a flat shape, which not only makes it easy to carry, but also makes it possible to provide diverse designs.

In conventional delivery apparatus for medical fluids, as shown in FIG. 7, utilizing a tubular body, a tubular body (300) is inserted into a pipe conduit (200) usually furnished with a channel, whereby in a state in which the tubular body is closely adhered to the pipe conduit, the medical fluid injected through the pipe conduit (400) enters into the tubular body through the channel and causes the tubular body, made of one layer, to expand.

Therefore, the expanded tubular body (300) allows a medical fluid to be discharged with a strong pressure in the beginning, but, as time passes, the expanded, one-layered tubular body contracts, thereby causing the pressure to drop, and results in a decrease in the volume of medical fluid being discharged, which is disadvantageous.

Accordingly, due to such structural shortcoming, when inserting the conventional tubular body into the pipe conduit, the tubular body is in a tightly-stretched state, that is, tightly-fitted into the pipe conduit, the tubular body is stretched and tightly adhered to the pipe conduit by strong pressure that is to compensate for that variation of pressure in the beginning and later periods.

However, in such case not only is there a difficulty in assembly but also there are limitations in selecting material for the tubular body that does not change when it expands. And in such a case, there is a disadvantage of the initial pressure being too strong.

Moreover, another disadvantage is that it is impossible to offer variety in design since the shape of the final product is merely a simple pipe type.

Therefore, the present invention, having a tubular body wound up in two layers on a round projecting holder, and thereby maintaining constant pressure of the tubular body when expanded by the injection of medical fluid, in the beginning and later periods, solves, the problems of the prior arts and also makes it possible to offer a variety in design.

BRIEF DESCRIPTION OF THE DRAWINGS

Accompanying the specification are figures which assist in illustrating the embodiments of the invention, in which.

DETAILED DESCRIPTION OF THE INVENTION

Embodiments of the apparatus of the present invention are described in detail below referring to the attached drawings.

In one embodiment of the present invention, the structure an upper case (10) and lower case (20), which are assembled as counterparts, and such counterpart assembly enables detaching.

Additionally, this embodiment of the apparatus is equipped with a separate intermediate ring (30) of specific width, in between of the upper case (10) and the lower case (20), which not only enables easy assembly and a variety of designs, but also adjustment of the volume of medical fluid capable of being contained, according to the width of the intermediate ring.

Figure 1:
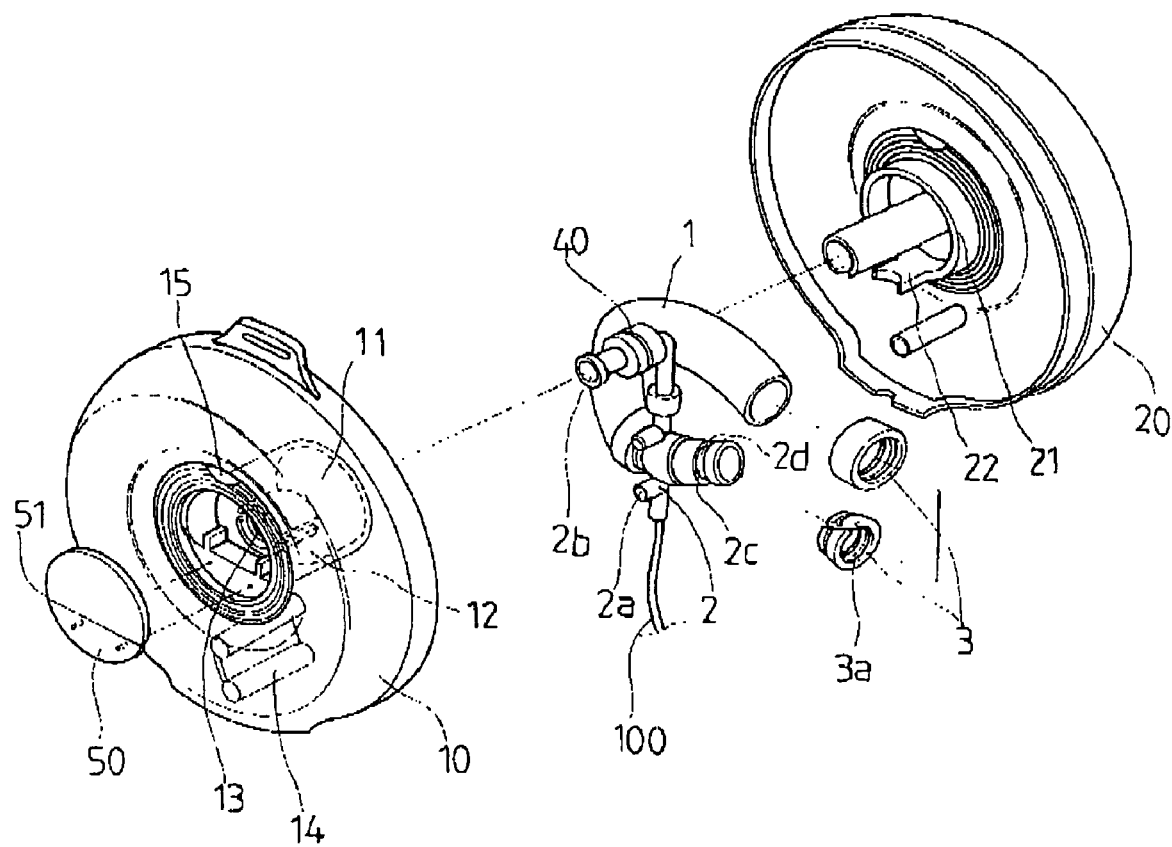
FIG. 1 is a perspective view showing an example of the assembled structure of the invention.

As shown in FIG. 1, this invention includes an upper case (10), wherein a projecting holder (11) is formed in the center of the upper case (10) for the tubular body to be wound upon, a tubular body (1) of which both ends are connected to each other and affixed to a branch conduit (2) by affixation member (3), in order to wind onto the projecting holder (11), and a hose (100) is connected to the branch conduit for the flow of medical fluid. At the branch conduit 2, an injection port for injection of medical fluid is formed and is exposed to the outside of the case.

Additionally, the inner wall of the lower case (20) adheres in parallel as tightly as possible to, or occludes in the tightly-adhered stated with, the projecting holder (11) of the upper case (10) to prevent the tubular body (1), wound on the projecting holder (11), from separating and being crushed. An open groove (12) formed on the supporting projecting holder (11) which has a bore wide enough for the branch conduit (2) to fit is formed to affix the branch conduit (2). In order to prevent the branch conduit (2) fitted in to above open groove (12) from separating, a protrusion (22) is formed at the lower case (20) to occlude with the open groove (12). The open groove (12) is equally divided between the upper case (10) and the lower case (20), with which it combines, and that allows for secure affixing by application of pressure.

Since this is an already known method, a variety of methods can be proposed.

And an injection port (2b) is formed on the branch conduit (2) and is combined with an injection valve (40) that has one directional flow, whereby the injection valve (40) is exposed through a passageway hole (13) of the upper case (10) and thereafter, medical fluid is injected through the injection valve (40) which is exposed through the passageway hole (13). Therefore, medical fluid, when injected into the injection port (2b), flows into the branch conduit (2) and expands the tubular body (1). Since the expanded two-layered tubular body (1) tightly adheres to the projecting holder (11) and winds circularly therearound, it contracts with the two layers at the same time when contracting and thereby, the change of its expansion pressure in the beginning and later periods becomes reduced.

Figure 2:
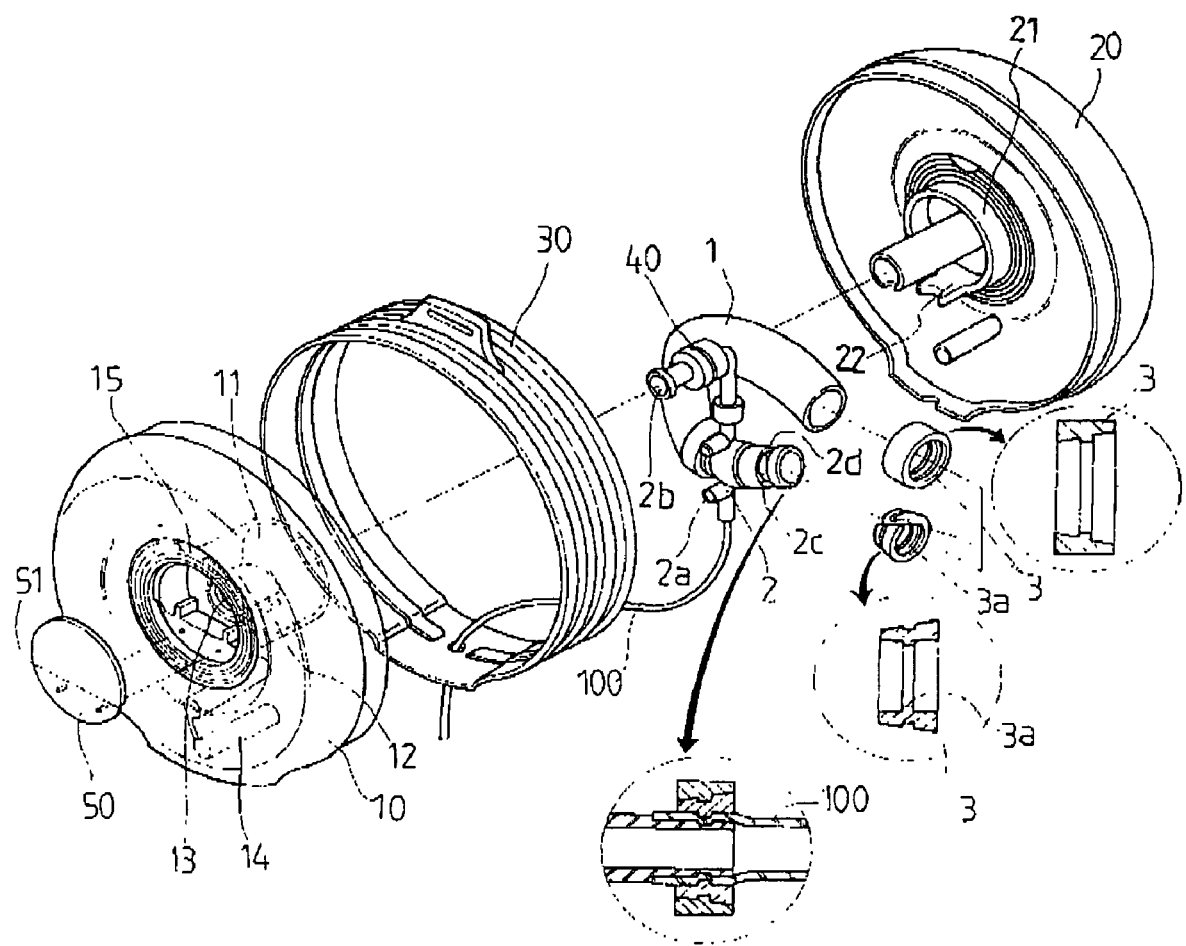
FIG. 2 is a perspective view showing another example of the assembled structure.
Figure 3:
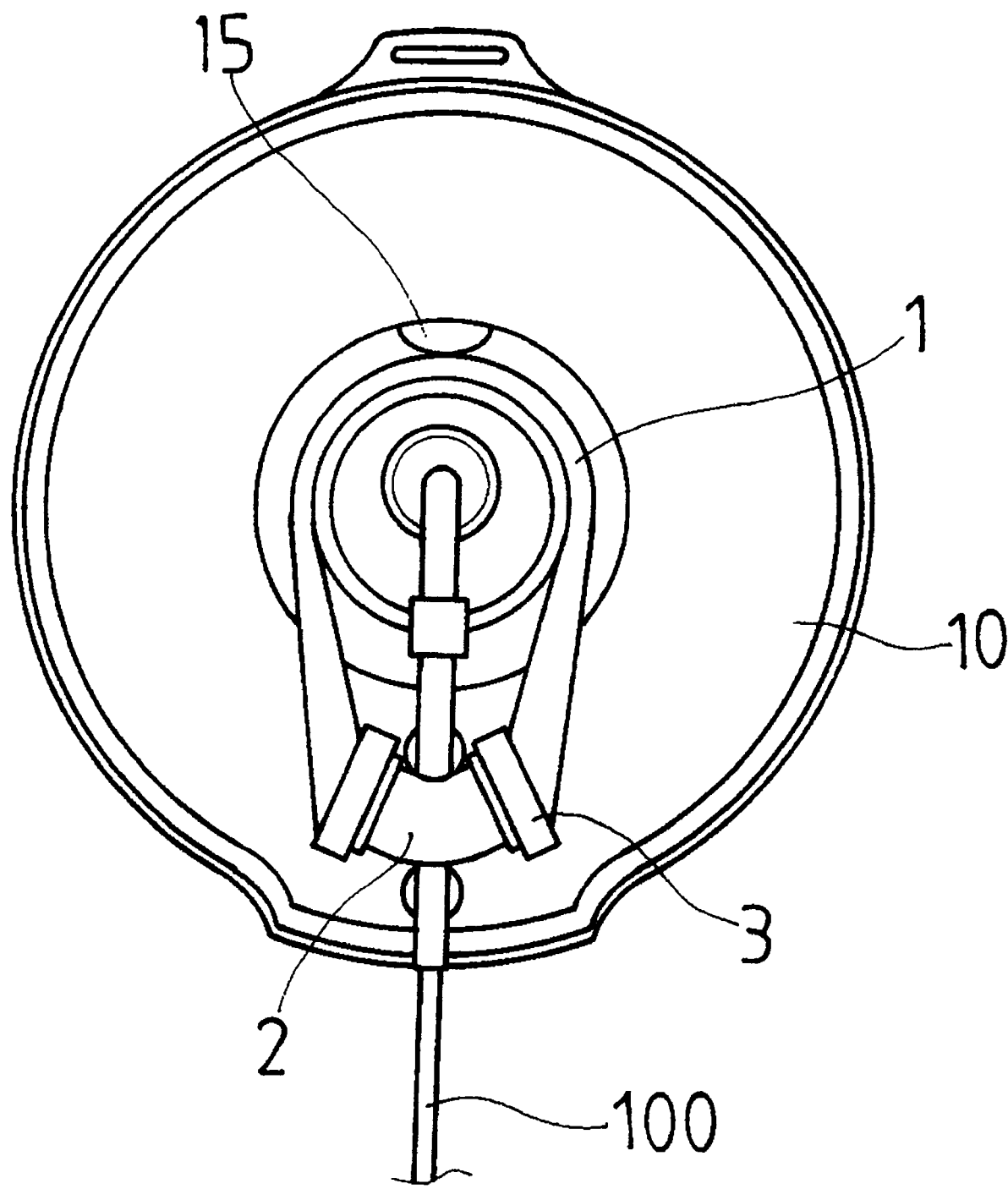
FIG. 3 is a plan view showing affixation of a tubular-body in a stretched state.
Figure 4:
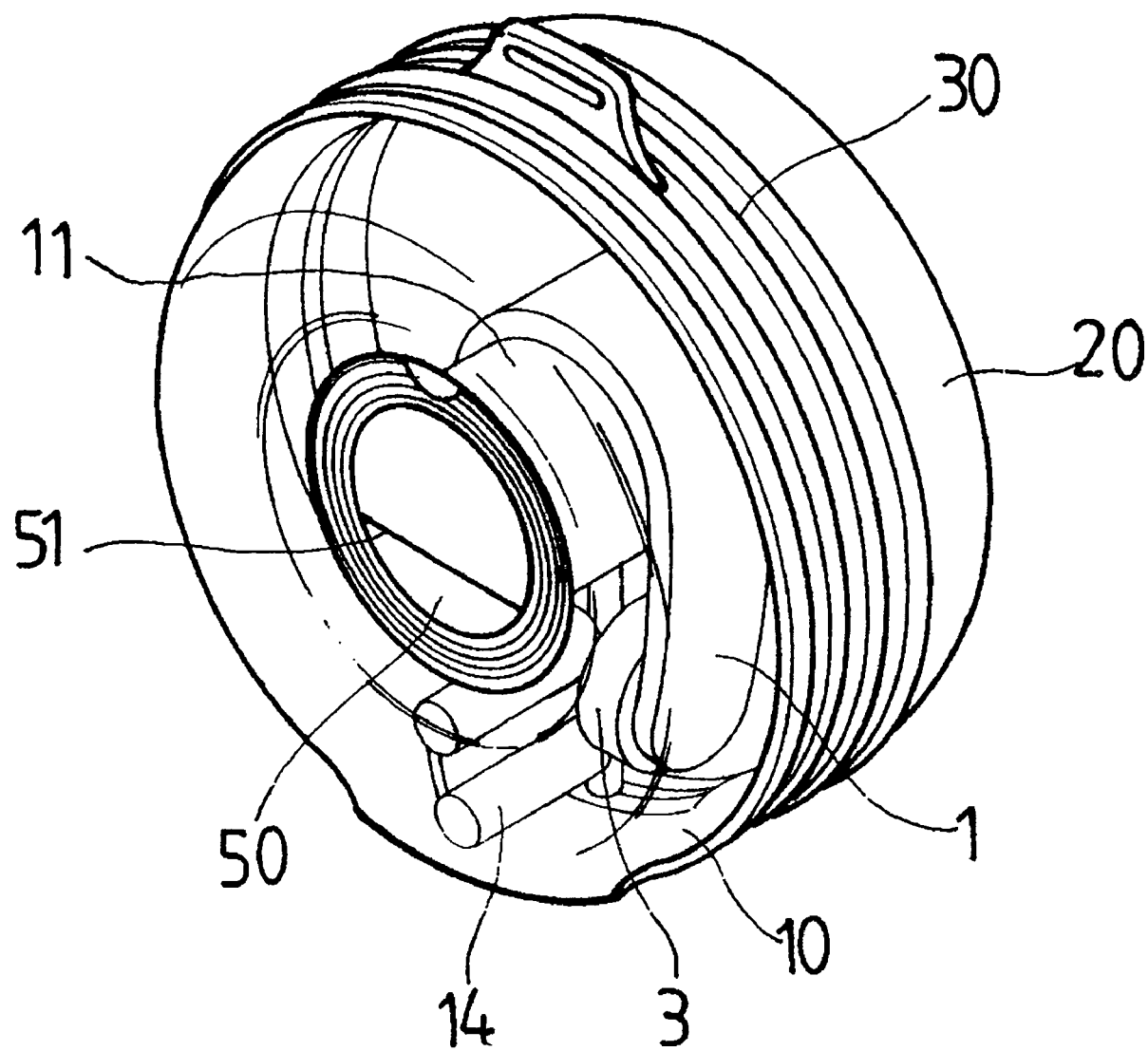
FIG. 4 is a perspective view showing the outer appearance of the assembly.
Figure 5:
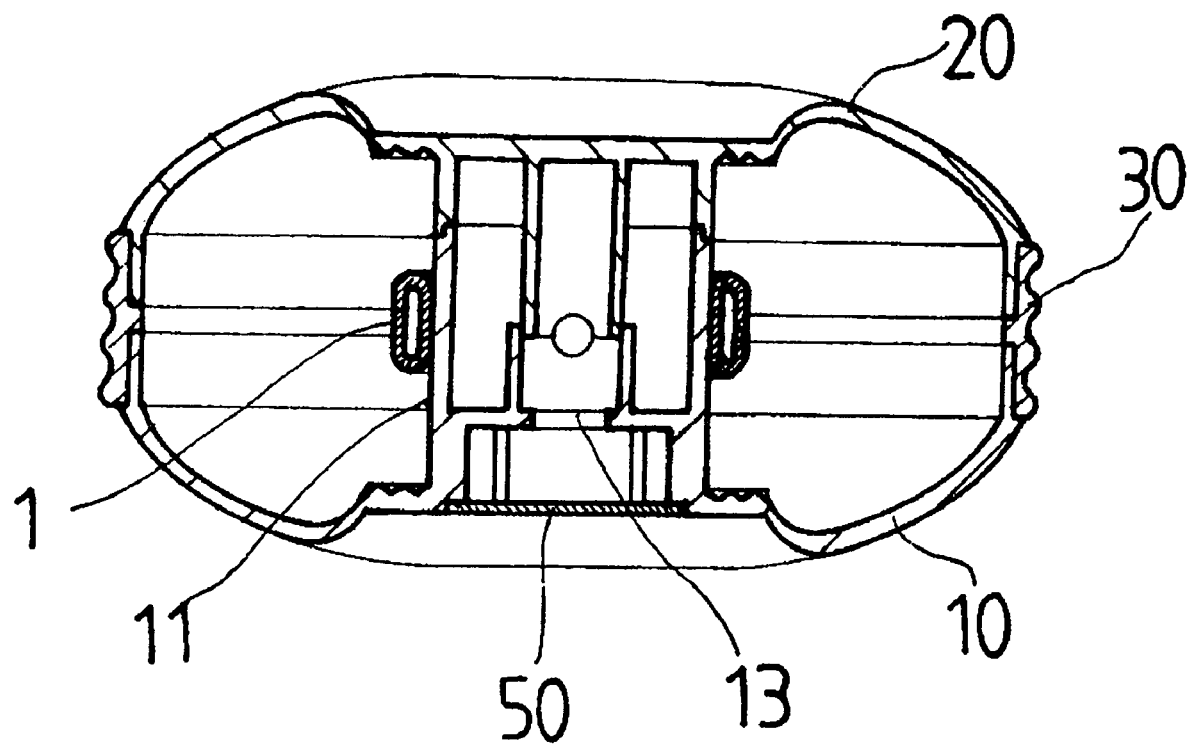
FIG. 5 is a cross-sectional view showing an upper case and a lower case, connected with an intermediate-ring.
Figure 6:
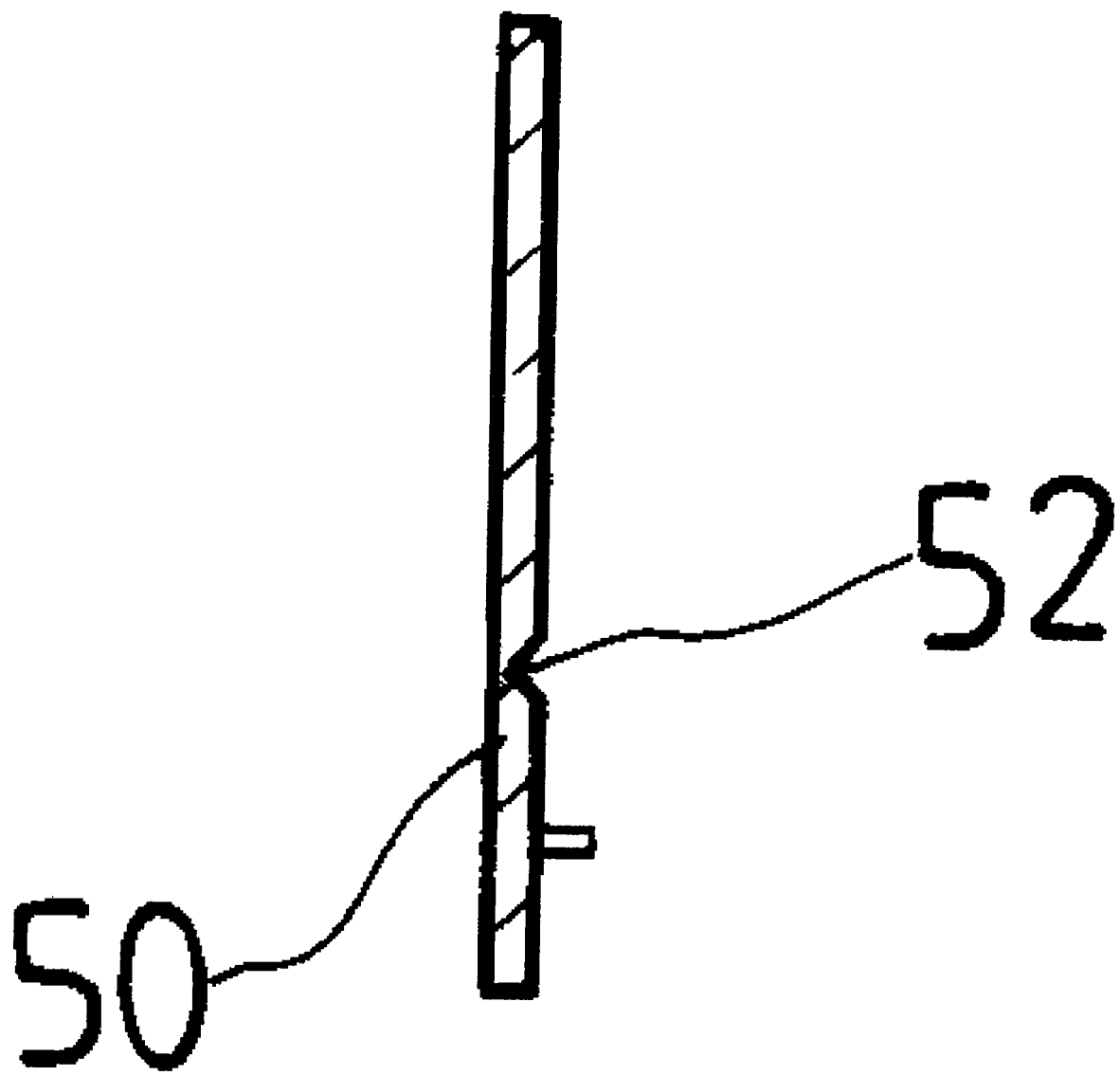
FIG. 6 is a cross-sectional view of a lid.
Figure 7:
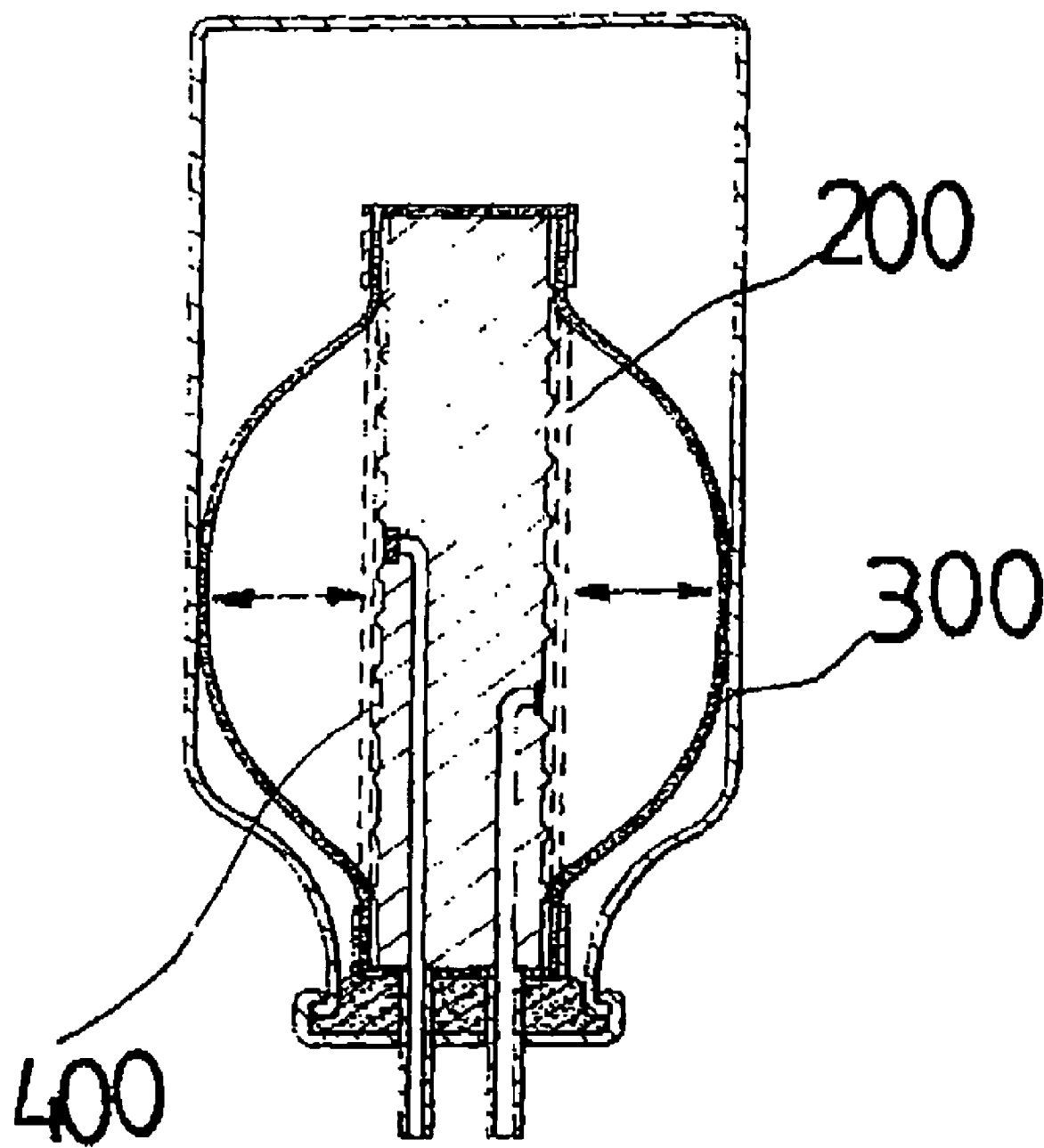
FIG. 7 is a cross-sectional view of the prior art.

Furthermore, as shown in FIG. 2, when an intermediate ring of a specific width is employed between the aforementioned upper case (10) and lower case (20), it is not necessary to prepare additional upper cases (10) and lower cases (20) for situations of different injection volume of medical fluids. By varying the width of the intermediate ring, it is easy to change its shape according to the different volumes, and thus being able to immediately deliver upon the demand of consumers is its advantage. And it is also possible to offer a variety of designs by making the intermediate ring (30) in various colors.

Additionally, the combining method to affix the branch conduit (2) is by forming fixing protrusion (2a) on the branch conduit (2) and by forming fixing grooves (14) on the counter parts of the upper case (10) and lower case (20), which thereby allow firm affixation by combining upon applying force.

A lid (50), which opens and closes when pressed, is formed in order to cover the passageway hole (13) of the upper case (10) for preventing outside foreign material from entering.

The lid (50) used herein has a scored folding line (51), on the inside of which is formed a slot (52) of V-shape, and the inner side of the scored folding line (51) is fixed to the upper case, so that the outer side is raised to open and close, when the scored folding line is pressed, and a tip of the outer side combines wit the upper case (10) having a stopper (15) to allow the passageway hole (13) to open and close.

There is a variety of known methods for the manufacture of a stopper, wherein the stopper can be formed on the lid.

The branch conduit (2), to which both ends of the tubular body (1) is connected and fixed, is made out of material that does not expand due to the injection of medical fluids. A variety of known methods can be used to affix the tubular body (1) connected to such branch conduit (2).

However, affixing with an additional affixation member (3), with double sheathing, if possible, is necessary in order to prevent it from detaching or cracking, while in a fixed state, due to expansion pressure, and such double sheathing is possible whether its material is made of the same or a different material as that of the tubular body.

Additionally, to prevent detaching, on the branch conduit (2) is formed a recess groove (2c) which is sufficiently large enough to allow the affixation member (3) to be inserted through, and on the recess groove is further formed a rabbet groove (2d), which a projecting ring (3a), formed on the affixation member, is fitted into and affixed, and that prevents detaching.

Furthermore, as shown in FIG. 1, by forming the affixation member in two-layers, and in order to induce an elastic operation in a situation where the affixation member is made out of stiff material, and by having the inside of the affixation member incised and the outside not incised, enables solid affixation.

Additionally, when such affixation member is double sheathed, using the same material as that with which the tubular body is made, and afterward is also fixed using a fixing band, it has the same effect of affixation.

When pressure is applied for affixing, the skin of part of the tubular body becomes thin, which could expand and crack when pressure is delivered for injection of medical fluid. Double sheathing can solve such a problem.

The present invention may be embodied in other specific forms without departing from its spirit or essential characteristics. The described embodiments are to be considered in all respects only as illustrative and not as restrictive. The scope of the invention is, therefore, indicated by the appended claims and their combination in whole or in part rather than by the foregoing description. All changes that come within the meaning and range of equivalency of the claims are to be embraced within their scope.

The invention claimed is:

1. A delivery apparatus for medical fluids, comprising:
   an outer casing including an upper case and a lower case;
   a tubular body having opposed ends connected with one another, said tubular body being expandable and contractible such that said tubular body expands when medical fluids are injected into said tubular body, and said medical fluids are expelled by pressure produced by subsequent contraction of said tubular body;
   a branch conduit connectably joining said opposed ends of said tubular body to one another, said branch conduit including an injection port for injection of medical fluids into said tubular body, said injection port being exposed to an outside of said upper case;
   a projecting holder being integrally formed with said upper case at a center of said upper case so as to be disposed centrally of an interior of said outer casing said projecting holder extending axially between said upper and lower cases, said tubular body being circumferentially wound about said projecting holder, an inner wall of said lower case being tightly fitted in parallel to the projecting holder so as to occlude or eliminate any space therebetween to thereby prevent the tubular body wound on the projecting holder from separating and being crushed, said projecting holder including a groove dimension with a width sufficient to fittably receive said branch conduit and said lower case includes an internally disposed protrusion which faces said branch conduit so as fix the branch conduit in place within said groove; and
   a hose for delivery of the medical fluids extending through said outer casing and connecting to said branch conduit within said outer casing.

2. The apparatus according to claim 1, further comprising an intermediate ring being interposed between said upper case and said lower case allowing an internal volume of said outer casing to be determined by selection of a particular width of said intermediate ring.

3. The apparatus according to any one of claims 1 and 2, further comprising:
   axially extending fixing protrusions disposed on said branch-conduit, for affixing said branch-conduit; and
   corresponding axially extending fixing grooves disposed on at least one of said upper case or said lower case, which cooperate with and fix corresponding ones of said fixing protrusions for axially fixing said tubular body within said outer casing, said protrusions and said grooves being disposed within said outer casing.

4. The apparatus according to any one of claims 1 and 2, further comprising a unidirectional flow injection valve in fluid communication with both said injection port and a passageway hole in said upper case.

5. The apparatus according to claim 1, wherein said tubular body is wound onto said projecting holder in a stretched state.

6. The apparatus according to claim 1, further comprising a recess groove formed on said branch-conduit, and wherein an affixing member is fixed by applying pressure to said recess groove.

7. The apparatus according to claim 6, further comprising a rabbet groove on said recess groove, and a projecting ring, which cooperates with said rabbet groove, on said affixing member.

8. The apparatus according to claim 6, wherein said recess groove of said branch conduit is doubly sheathed over said tubular body, and is affixed by pressure.

9. The apparatus according to claim 6, wherein said affixing member is formed in two layers, and an interior side of said affixing member is incised so as to be elastically reactive.

10. A delivery apparatus for medical fluids, comprising:
an outer casing including an upper case and a lower case;
a tubular body having opposed ends connected with one another, said tubular body being expandable and contractible such that said tubular body expands when medical fluids are injected into said tubular body, and said medical fluids are expelled by pressure produced by subsequent contraction of said tubular body;
a branch conduit connectably joining said opposed ends of said tubular body to one another, said branch conduit including an injection port for injection of said medical fluids into said tubular body, said injection port being exposed to an outside of said upper case;
a projecting holder being disposed centrally of an interior of said outer casing said projecting holder axially extending substantially an entire distance between said upper and lower cases, said tubular body being circumferentially wound about said projecting holder; and
a hose for delivery of the medical fluids expelled by the contraction of said tubular body, said hose extending through said outer casing and communicatively connecting to said branch conduit within said outer casing.

11. The apparatus according to clam 10, further comprising an intermediate ring being interposed between said upper case and said lower case allowing an internal volume of said outer casing to be determined by selection of a particular width of said intermediate ring.

12. The apparatus according to claim 10, wherein said tubular body is circumferentially wound about said projecting holder with sufficient tightness to at least partially flatten a cross-section of said tubular body about said projecting holder and adhere the tubular body to the projecting holder.

13. The apparatus according to claim 10, wherein:
said projecting holder is integrally formed with said upper case at a center of said upper case; and
an inner wall of said lower case is tightly fitted in parallel to the projecting holder so as to occlude or eliminate any space therebetween to thereby prevent the tubular body wound on the projecting holder from separating and being crushed.

14. The apparatus according to claim 10, wherein:
said projecting holder includes a groove dimensioned with a width sufficient to fittably receive said branch conduit; and
said lower case includes an internally disposed protrusion which faces said branch conduit so as to fix the branch conduit in place within said grove.

15. The apparatus according to claim 10, wherein said tubular body is wound onto said projecting holder in a stretched state sufficient to compensate for a reduction pressure as said tubular body contracts to a state before expansion thereof while expelling the medical fluids.

16. The apparatus according to claim 10, further comprising a unidirectional flow injection valve in fluid communication with both said injection port and a passageway hole in said upper case.

17. The apparatus according go claim 16, further comprising a press-operable and closeable lid, for alternatively opening and closing said passageway hole of said upper case.

18. The apparatus according to claim 17, wherein:
said lid has a scored folding line on an exterior side of said lid and a V-shaped slot on an interior side of said lid;
a portion of said lid below said scored folding line is affixed to said upper case; and
said exterior side of said lid is raised when said scored folding line is pressed, to enable said lid to open and close.

* * * * *